United States Patent [19]

Fisch et al.

[11] Patent Number: 4,650,894
[45] Date of Patent: Mar. 17, 1987

[54] TRIS-ORGANOPHOSPHITE COMPOSITIONS HAVING IMPROVED HYDROLYTIC STABILITY

[75] Inventors: Michael H. Fisch, Wayne; Barbara A. Hegranes, Pompton Plains, both of N.J.; George A. Seubert, Jr., Massapequa Park, N.Y.

[73] Assignee: Argus Chemical Corporation, Brooklyn, N.Y.

[21] Appl. No.: 627,956

[22] Filed: Jul. 5, 1984

[51] Int. Cl.$^4$ .......................................... C07F 9/143
[52] U.S. Cl. ...................................................... 558/71
[58] Field of Search .................. 260/989; 524/153; 558/71

[56] References Cited

U.S. PATENT DOCUMENTS

| | | | |
|---|---|---|---|
| 3,553,298 | 1/1971 | Hodan et al. | 260/967 |
| 3,787,537 | 1/1974 | Marcq | 260/989 |
| 3,922,249 | 11/1975 | Mills | 564/506 |

*Primary Examiner*—Anton H. Sutto

[57] ABSTRACT

Tris-organophosphite compositions are provided having an improved hydrolytic stability, comprising (1) a tris-organophosphite of the formula:

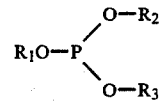

I wherein:

$R_1$, $R_2$ and $R_3$ are selected from the group consisting of alkyl, alkenyl, aryl, alkylaryl and aralkyl groups together aggregating at least fourteen carbon atoms up to about sixty carbon atoms; and (2) a long-chain aliphatic amine in an amount to improve the hydrolytic stability of the phosphite and having the formula:

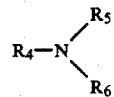

II wherein:

$R_4$, $R_5$ and $R_6$ are selected from the group consisting of hydrogen; aliphatic (including alkyl and alkenyl) groups having from one to about thirty-six carbon atoms; and hydroxyalkyl having from two to about six carbon atoms; one of $R_4$, $R_5$ and $R_6$ is an aliphatic group having at least ten carbon atoms, and the remaining of $R_4$, $R_5$ and $R_6$ are selected from hydrogen, alkyl having from one to four carbon atoms and hydroxyalkyl; and preferably at least one of $R_4$, $R_5$ and $R_6$ is hydroxyalkyl.

13 Claims, No Drawings

TRIS-ORGANOPHOSPHITE COMPOSITIONS HAVING IMPROVED HYDROLYTIC STABILITY

Many organic phosphites have been proposed as stabilizers for polyvinyl chloride resins, and are employed either alone or in conjunction with other stabilizing compounds, such as polyvalent metal salts of fatty acids and alkyl phenols. Such phosphite stabilizers normally contain alkyl or aryl radicals in sufficient number to satisfy the three valences of the phosphite, and typical phosphites are described in the patent literature, for example, W. Leistner et al, U.S. Pat. Nos. 2,564,646 of Aug. 14, 1951, 2,716,092 of Aug. 23, 1955 and 2,997,454 of Aug. 2, 1961.

Organic phosphites have also been added as stabilizers in amounts of 0.01 to 1%, preferably 0.05% to 0.2% by weight, to high molecular weight polycarbonate plastics, for example the polycarbonate of 2,2'-bis(4-hydroxyphenyl)propane.

Phosphites are also employed in conjunction with other stabilizers such as a polyhydric phenol in the stabilization of polypropylene and other synthetic resins against degradation upon heating or ageing under atmospheric conditions. The polyhydric phenol is thought to function as an antioxidant in such combinations.

The importance of organic phosphites as stabilizers for synthetic resins has led to the development of a large variety of special phosphites intended to provide improved stabilizing effectiveness and compatibility and ease of compounding with the resin and with other stabilizers commonly used.

Among these special phosphites, L. Friedman, U.S. Pat. No. 3,047,608 of July 31, 1962 discloses a class of spiro-biphosphites having the formula:

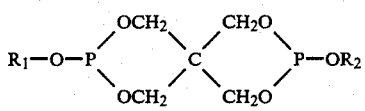

in which $R_1$ and $R_2$ are alkyl or aryl.

Hechenbleikner, U.S. Pat. No. 4,290,976, patented Sept. 22, 1981, states that dialkyl pentaerythritol diphosphites having the structural formula

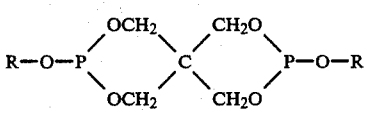

where R and R are alkyl groups have been known for some time as effective stabilizers for vinyl polymers. They have been used primarily to stabilize vinyl chloride polymers and polyolefins, but have found use also in the stabilization of styrene polymers such as ABS.

However, these dialkyl pentaerythritol diphosphites have not been characterized by good hydrolytic stability. In a moist environment they tend to undergo hydrolytic decomposition, with a corresponding loss of polymer-stabilizing effectiveness. Attempts to solve this problem of hydrolysis have utilized additives and these have been somewhat successful, but the problem remains, according to Hechenbleikner.

Hodan and Schall, U.S. Pat. No. 3,553,298, patented Jan. 5, 1971 suggested that the hydrolytic stability of phosphite esters of a wide class could be improved by combination therewith of an additive that is nitrogen-containing and selected from the group consisting of heterocyclic alkyl nitrogen compounds, such as typically piperidine, pyrrolidine, piperazine, diketopiperazine, picoline, anthraquinoline, N-methyl pyrrolidine, thiazole, oxazolidine, isooxazolidine, and oxdiazole; aromatic heterocyclic nitrogen compounds, such as typically oxazoline, isoxazoline, thiotriazole, pyridine, picoline, pyrrole, and quinoline; dialkanolamines such as typically diisopropanol amine, diethanol amine, tetraethanol ethylene diamine, and tetraisopropanol ethylene diamine; trialkanol amines such as typically triisopropanol amine, and triethanol amine; ammonia; and alkyl amines such as triethyl amine, dimethyl amine, and tripropyl amine.

The stabilizer is normally employed in from about 0.01% to about 5% by weight of the phosphite ester, preferably from about 0.2% to about 1%.

York, U.S. Pat. No. 4,116,926, patented Sept. 26, 1978 found triisopropanolamine to be a particularly effective stabilizer for dialkylpentaerythritol diphosphites and polyalkyl bisphenol-A polyphosphites.

The dialkylpentaerythritol diphosphites have the structural formula:

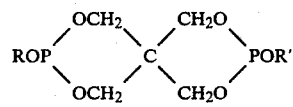

where R and R' are alkyl groups. The polyalkyl bisphenol-A polyphosphites have the structural formula:

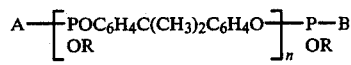

where A and B are each $HOC_6H_4C(CH_3)_2C_6H_4O$ or RO. R is alkyl and n is 1 to 5.

Most alkyl and alkylaryl pentaerythritol-spiro-bis phosphites having fourteen or more carbon atoms in the alkyl or alkylaryl groups and indeed even pentaerythritol-spiro-bis phosphite itself are solid materials. When their melting point is above 40° C., they are readily reduced to particulate form, and therefore are easily blended with other solid stabilizers for combination with synthetic resins. When however triisopropanolamine is used to improve hydrolytic stability, the desirable qualities of these pentaerythritol-spiro-bis-phosphites as an easily-handled particulate solid material are lost, and the material is converted into a sticky solid that is rather difficult to work with. It is not readily reduced to particulate form, and when in particulate form tends to agglomerate with itself and with other materials that are sought to be blended therewith, in formulating multicomponent stabilizer systems.

In accordance with Ser. No. 542,923 filed Nov. 28, 1983, long-chain aliphatic amines are shown to be effective in improving the hydrolytic stability of pentaerythritol-spiro-bisphosphites, and in addition are readily formulated therewith to form nonsticky solid compositions that are readily reduced to particulate form, and can easily be blended with other stabilizers and with synthetic resins, thus overcoming the stickiness problem inherent in the use of triisopropanolamine.

The pentaerythritol-spiro-bis-phosphite compositions of Ser. No. 542,923 having an improved hydrolytic stability consist essentially of (1) a pentaerythritol-spiro-bis-phosphite having the formula:

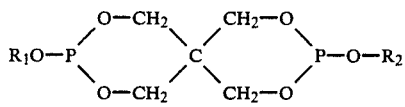

wherein:

$R_1$ and $R_2$ are selected from the group consisting of alkyl and alkylaryl groups having at least fourteen carbon atoms up to about thirty-six carbon atoms; and (2) a long-chain aliphatic amine in an amount to improve the hydrolytic stability of the phosphite and having the formula:

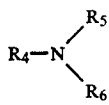

wherein:

$R_4$, $R_5$ and $R_6$ are selected from the group consisting of hydrogen; aliphatic (including alkyl and alkenyl) groups having from one to about thirty-six carbon atoms; and hydroxyalkyl having from two to about six carbon atoms; one of $R_4$, $R_5$ and $R_6$ is an aliphatic group having at least fourteen carbon atoms, and the remaining $R_4$, $R_5$ and $R_6$ are selected from hydrogen, alkyl having from one to four carbon atoms and hydroxyalkyl; and preferably at least one of $R_4$, $R_5$ and $R_6$ is hydroxyalkyl.

In accordance with the present invention, it has been determined that such long-chain aliphatic amines also improve the stability of tris-organophosphites of the formula:

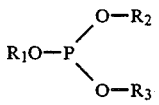

wherein:

$R_1$, $R_2$ and $R_3$ are selected from the group consisting of alkyl, alkenyl, aryl, alkylaryl and aralkyl groups together aggregating at least fourteen carbon atoms up to about sixty carbon atoms.

The improvement in hydrolytic stability of the tris-organophosphite is evident with the addition of even small amounts, as little as 0.1%, of the aliphatic amine. The improvement increases with the amount of amine added. In most instances amounts within the range from about 2% to about 3.5% and even up to about 10% of the amine give adequate hydrolytic stability for normal use. Such amounts are therefore preferred. Larger amounts of amine can be used but tend to be wasteful and uneconomic.

Exemplary $R_4$, $R_5$ and $R_6$ alkyl groups in the amines include, for example, methyl, ethyl, propyl, isopropyl, butyl, secondary butyl, tertiary butyl, isobutyl, amyl, isoamyl, secondary amyl, 2,2-dimethyl propyl, tertiary amyl, hexyl, isohexyl, heptyl, octyl, 2-ethyl hexyl, isooctyl, nonyl, isononyl, decyl, isodecyl and lauryl. The following are also exemplary of $R_1$, $R_2$ and $R_3$ in the phosphite as well as $R_4$, $R_5$ and $R_6$ in the amines: myristyl, palmityl, stearyl, oleyl, eicosyl, behenyl, tricosyl, tetracosyl, octacosyl, nonacosyl, triacontyl, hentriacontyl, tritriacontyl, and hexatriacontyl.

$R_1$, $R_2$ and $R_3$ alkaryl and aralkyl groups in the phosphite include benzyl, phenethyl, phenylpropyl, phenylbutyl, phenylamyl, phenyloctyl, phenylnonyl; methylphenyl, ethylphenyl, propylphenyl, butylphenyl, amylphenyl, tert-butyl phenyl, tert-amyl phenyl, hexyl phenyl, octylphenyl, 2,6-di-t-butyl-4-methylphenyl, 2,6-di-t-butyl-4-(methoxycarbonylethyl phenyl, isooctylphenyl, t-octylphenyl, nonylphenyl, 2,4-di-t-butylphenyl, benzylphenyl and phenethylphenyl.

Tris organophosphites include tris-nonyl phenyl phosphite, nonylphenyl di-isopropyl phosphite tri-2-ethylhexyl phosphite, triisodecyl phosphite, tris-hexadecyl phosphite, tris-stearyl phosphite, diphenyl isooctyl phosphite, di-isodecyl phenyl phosphite, tris(2,4-di-t-butylphenyl)phosphite, tris-(2,6-di-t-butylphenyl)-phosphite, tris-(2-t-butyl-4-methylphenyl)phosphite, bis-(2,4-di-t-butyl-6-methylphenyl)octylphenyl phosphite, bis(2,4-di-t-butyl-6-methylphenyl)nonylphenyl phosphite, bis-(2,6-di-t-butyl-4-methylphenyl)phenyl phosphite, bis(2,6-di-t-butyl-4-ethylphenyl)octyl phosphite, nonylphenyl 2,6,di-t-butyl-4-methylphenyl-2,6-di-t-butylphenyl phosphite, octyl 2,6-di-t-butyl-4-methylphenyl 2,4-di-t-butylphenyl phosphite, dodecyl 2,6-di-t-butyl-4-methylphenyl-2,4-di-t-octylphenyl phosphite, tris(2,6-di-t-amyl-4-methylphenyl phosphite, bis(2,6-di-t-amyl-4-methylphenyl)phenyl phosphite, bis(2,6-di-t-octyl-4-methylphenyl)nonylphenyl phosphite, tri-isoamyl phosphite, triphenyl phosphite, tri-n-hexyl phosphite, and isodecyl diethyl phosphite.

The tris-organophosphite/long-chain aliphatic amine compositions of the invention can be prepared by blending the tris-organophosphite and long chain aliphatic amine in any convenient manner. Liquid phosphites can be blended with the aliphatic amine at ambient temperature or warmed gently to diminish viscosity and speed up mixing. When the phosphite is solid at ambient temperature and molten below about 110° C., the aliphatic amine is conveniently mixed into the melt before allowing the composition to solidify. A relatively high melting phosphite can be blended with the amine with the assistance of a mutual solvent such as toluene or isopropanol. Alternatively, the particulate phosphite can be tumbled or agitated with the aliphatic amine in molten or particulate form.

Complete homogenization of the phosphite and amine composition is not essential. In fact, a condition in which a large part of the aliphatic amine is concentrated at or near the surface of solid phosphite particles as in a coating or encapsulation desirably maximizes the effectiveness of the amine when used in modest concentrations, such as 5% by weight of the phosphite.

Exemplary alkyl monoalkanol amines, which are a preferred class of aliphatic amines, include palmityl ethanolamine, lauryl ethanolamine, isodecyl ethanolamine, stearyl ethanolamine, oleyl ethanolamine, myristyl ethanolamine, behenyl ethanolamine, and eicosyl ethanolamine; stearyl propanolamine, palmityl propanolamine, distearyl monoethanolamine, dipalmityl monoethanolamine, dimyristyl monoethanolamine, and myristyl propanolamine.

Exemplary alkyl dialkanol amines, which are also a preferred class of aliphatic amines, include palmityl diethanolamine, stearyl diethanolamine, oleyl diethanolamine, myristyl diethanolamine, behenyl diethanolamine, eicosyl diethanolamine; stearyl dipropanolamine, palmityl dipropanolamine, myristyl dipropanolamine, n-decyl diethanolamine, and lauryl diethanolamine.

Exemplary trialkyl amines include stearyl diethylamine, myristyl diethylamine, palmityl diethylamine, stearyl decyl octyl amine, stearyl butyl decyl amine, distearyl ethylamine, dipalmityl propylamine, behenyl dimethylamine and isodecyl dibutylamine.

Exemplary dialkyl amines include stearyl ethyl amine, myristyl ethyl amine, palmityl ethyl amine, stearyl decyl amine, stearyl butyl amine, stearyl methyl amine, palmityl propyl amine, behenyl methyl amine, and eicosyl methyl amine.

Exemplary monoalkyl amines include stearyl amine, myristyl amine, palmityl amine, oleyl amine, and behenyl amine.

The following Examples illustrate tris-organophosphite compositions having an improved hydrolytic stability in accordance with the invention.

EXAMPLES 1 TO 4

To tris-nonylphenyl phosphite was added N-tallow diethanolamine (90% C-18, balance mainly C-16) in the amounts listed in Table I below. Homogeneous liquid blends were obtained in each Example.

The hydrolytic, stability of the phosphite compositions was determined in terms of the days required for 50% decomposition to occurs as a 1.5 gram sample of each phosphite composition was exposed in a humidity chamber at 100% relative humidity. The exposed phosphite composition was sampled periodically and analyzed by liquid chromatography. The following procedure was used.

A humidity chamber was set up using a large desiccator (SGA No. 1230, 250 mm) with double-tiered plates. In the desiccator's well were put 1500 ml of water to obtain 100% RH.

In aluminum weighing dishes (SGA No. 9000) there was placed the indicated quantity of the composition and, at a time zero, the dishes were placed inside the humidity chamber. Simultaneously, a LC analysis was run at time zero. Later, on withdrawing samples for sequential LC analyses the composition was thoroughly mixed inside the aluminum dish using a spatula, before withdrawing the actual sample.

In a 2-gram vial (SGA No. 5250) there were weighed accurately 20 mg of sample, also a micromagnetic stirring bar and 5 ml. (accurately measured) of the LC solvent used (see below). The mixture was stirred for 10 minutes on a magnetic stirring plate and filtered using a Sample Clarification Kit (Waters catalog No. 26865). Exactly 10 mcl of the filtered solution was injected using the LC parameters indicated below.

LIQUID CHROMATOGRAPHY

LC runs were carried out using a duPont modified-silica Zorbax-CN column (duPont No. 850952-705). Solvent, a 10-1 (v-v) mixture of isooctane-THF (LC grade), pumped at the rate of 1 ml/min. Chart speed: 0.5"/min.; detectors: Refractive Index att. ×4 and U.V. (254 nm) at att. ×0.1 AUFS.

CALCULATIONS

All calculations were carried out on the RI trace obtained. Peak heights were measured (in mm.) from the base line. A "Response factor, f" was calculated for each peak, using this equation $$f = \frac{\text{peak height (mm)}}{\text{weight (mg)} \times 2}$$

This equation applies only when the weight is dissolved in 5-ml. of solvent and 10 mcl. are injected.

The change of "f" with time was followed. After total hydrolysis, the f values were normalized, assigning a value of 100 to the f value for the sample at time zero. The normalized values were plotted vs. time (in hours or days as indicated) to obtain the 50% decomposition time.

The following results were obtained:

TABLE I

| Example No | Amount of N—tallow diethanolamine % by weight of phosphite | Hydrolytic stability (Days to 50% decomposition)* |
| --- | --- | --- |
| Control | None | Less than one day |
| 1 | 1 | 3 days |
| 2 | 3 | 10 days |
| 3 | 5 | Over 143 days without change |
| 4 | 1 + epoxy soybean oil 5% | Over 60 days without change |

*100% RH, 1.5 g samples

As shown in Table I, the improvement by hydrolytic stability was commensurate with the amount of amine additive. Example 1, the composition containing 1% N-n-octadecyl diethanolamine, gave a hydrolytic stability that was adequate to normal use. Example 2, the composition containing 3% of the amine, gave generous protection even for extreme conditions. Example 3, the composition containing 5% amine, and Example 4, the composition containing 1% amine together with 5% epoxidized soybean oil, gave a dramatic further improvement in hydrolytic stability as compared to the compositions containing 1% or 3% of the amine.

These results are far superior to those obtained using prior art additives. To the same tris nonylphenyl phosphite used in Examples 1 to 4 were added the additives shown in Table II below:

TABLE II

| Example No. | Additive and % by weight of phosphite | Hydrolytic stability (days to 50% decomposition)* |
| --- | --- | --- |
| Control 1 | Epoxy soyabean oil 5% | 3 |
| Control 2 | Tri-isopropanol amine 0.5% | 3 |
| Control 3 | Tri-isopropanol amine 1% | 4 to 7 |
| Control 4 | Epoxysoyabean oil 5% +0.5% tri-isopropanol amine | 11 |
| Control 5 | Epoxysoyabean oil 5% +1% tri-isopropanol amine | 23 |

*100% RH, 1.25 g samples

As shown by comparing the results of Tables I and II, the hydrolytic stability of the phosphite has been dramatically improved by the addition of long chain amine in accordance with the invention.

In separate experiments it has been shown that the hydrolytic stability of tris-nonylphenyl phosphite is independent of exposed sample size in the range from 1 to 2 grams.

EXAMPLES 5 TO 11

N-coconut-alkyl diethanolamine (65% C-12, balance mainly C-14) was added to samples of various phosphites in the amounts listed in Table III below. Homogeneous liquid blends resulted in each Example.

The hydrolytic stability of the phosphite compositions was determined in terms of the days required for 50% decomposition to occur as 15 gram samples of each phosphite composition were exposed in a humidity chamber at 100% relative humidity. Each exposed phosphite composition was sampled periodically and analyzed for trivalent phosphorus P (III) by titration measuring the consumption of hydrogen peroxide as described in Hecker U.S. Pat. No. 3,056,824. In this titration, each of the triphosphites used consumes one mole of the oxidizing reagent $H_2O_2$ per mole of triphosphite while, on the other hand, hydrolytic fragments such as phosphorous acid, monoalkyl or monoaryl phosphites, diphosphites etc. do not consume the oxidizing reagent. The titration, therefore, represents a measure of how much of the starting triphosphite has been preserved during the elapsed time of exposure to 100% relative humidity.

The following results were obtained:

TABLE III

| Example | Phosphite | Amine[1] % by weight of phosphite | Epoxide[2] % by weight of phosphite | Initial % P(III) by titration | Hydrolytic Stability Days to 50% decomposition |
|---|---|---|---|---|---|
| 5 | Triphenyl phosphite | 1 | none | 9.45 | 5 |
| 6 | Triphenyl phosphite | 1 | 5 | 8.9 | 6 |
| Control A | | none | none | 9.6 | less than one day |
| 7 | 2-ethylhexyl diphenyl phosphite | 1 | 5 | 7.1 | 11 |
| Control B | | none | none | 7.5 | 3 |
| 8 | di-isodecyl phenyl phosphite | 1 | none | 6.0 | 5 |
| 9 | di-isodecyl phenyl phosphite | 3 | none | 6.2 | 9 |
| Control C | | none | none | 6.1 | 4 |
| 10 | tris-nonyl-phenyl phosphite | 1 | 5 | 3.8 | more than 37[3] |
| 11 | tris-nonyl-phenyl phosphite | 3 | 5 | 3.9 | more than 37[3] |
| Control D | | none | 5 | 3.9 | 15 |

[1]Amine = coconut-alkyl diethanolamine
[2]Epoxide = epoxysoybean oil
[3]On the 37th exposure day, titration showed more than 90% retention of P(III) and the experiment was stopped.

The results show the very considerable improvement in hydrolytic stability of each phosphite with coconut-alkyldiethanolamine compared to the same phosphite without the amine.

The phosphite amine compositions of the invention are effective, especially in combinations with other known stabilizers, in enhancing the resistance to deterioration by heat and light of polyvinyl chloride resins. The term "polyvinyl chloride" as used herein is inclusive of any polymer formed at least in part of the recurring group:

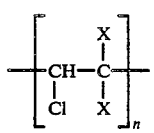

and having chlorine content in excess of 40%. In this group, the X groups can each be either hydrogen or chlorine, and n is the number of such units in the polymer chain. In polyvinyl chloride homopolymers, each of the X groups is hydrogen. Thus, the term includes not only polyvinyl chloride homopolymers but also after-chlorinated polyvinyl chlorides as a class, for example, those disclosed in British Pat. No. 893,288 and also copolymers of vinyl chloride in a major proportion and other copolymerizable monomers in a minor proportion, such as copolymers of vinyl chloride and vinyl acetate, copolymers of vinyl chloride with maleic or fumaric acids or esters, and copolymers of vinyl chloride with styrene. The stabilizer compositions are effective also with mixtures of polyvinyl chloride in a major proportion with a minor proportion of other synthetic resins such as chlorinated polyethylene or a copolymer of acrylonitrile, butadiene and styrene.

The phosphite and amine stabilizer compositions are applicable to the stabilization of rigid polyinvyl chloride resin compositions, that is, resin compositions which are formulated to withstand high processing temperatures, of the order of 375° F. and higher, as well as plasticized polyvinyl chloride resin compositions of conventional formulation, even though resistance to heat distortion is not a requisite. Conventional plasticizers well known to those skilled in the art can be employed, such as, for example, dioctyl phthalate, octyl diphenyl phosphate and epoxidized soybean oil.

Particularly useful plasticizers are the epoxy higher esters having from 20 to 150 carbon atoms. Such esters will initially have had unsaturation in the alcohol or acid portion of the molecule, which is taken up by the formation of the epoxy group.

Typical unsaturated acids are acrylic, oleic, linoleic, linolenic, erucic, ricinoleic, and brassidic acids, and these may be esterified with organic monohydric or polyhydric alcohols, the total number of carbon atoms of the acid and the alochol being within the range stated. Typical monohydric alcohols include butyl alcohol, 2-ethyl hexyl alcohol, lauryl alcohol, isooctyl alcohol, stearyl alcohol, and oleyl alcohol. The octyl alcohols are preferred. Typical polyhydric alcohols include pentaerythritol, glycerol, ethylene glycol, 1,2-propylene glycol, 1,4-butylene glycol, neopentyl glycol, ricinoleyl alcohol, erythritol, mannitol and sorbitol. Glycerol is preferred. These alcohols may be fully or partially esterified with the epoxidized acid. Also useful are the epoxidized mixtures of higher fatty acid esters found in naturally-occurring oils such as epoxidized soybean oil, epoxidized olive oil, epoxidized coconut oil, epoxidized cotton-seed oil, epoxidized tall oil fatty acid esters and epoxidized tallow. Of these, epoxidized soybean oil is preferred.

The alcohol can contain the epoxy group and have a long or short chain, and the acid can have a short or long chain, such as epoxystearyl acetate, epoxystearyl stearate, glycidyl stearate, and polymerized glycidyl methacylate.

The polyvinyl chloride resin can be in any physical form, including, for example, powders, films, sheets, molded articles, foams, filaments and yarns.

A sufficient amount of the phosphite and amine stabilizer composition is used to enhance the resistance of the polyvinyl chloride to deterioration in physical properties, including, for example, discoloration and embrittlement, under the heat and/or light conditions to which the polymer will be subjected. Very small amounts are usually adequate. Amounts within the range from about 0.01 to about 5% of the phosphite and from about 0.01 to about 10% of other stabilizers by weight of the polyvinyl chloride resin are satisfactory. Preferably, an amount within the range from about 0.05 to about 2% of phosphite, and from about 0.1 to about 5% of other stabilizer is employed for optimum stabilizing effectiveness.

The phosphite and amine stabilizer compositions of the invention can be employed as the sole stabilizers. They can also be used in combination with other conventional heat and light stabilizers for polyvinyl chloride resins, such as, for example, polyvalent metal salts and alkaline earth metal phenolates, as well as epoxy compounds.

A particularly useful stabilizer system contains the following amounts of ingredients:
(a) phosphite in an amount within the range from about 25 to about 45 parts by weight;
(b) phenolic antioxidant in an amount within the range from about 0.01 to about 1 part by weight;
(c) polyvalent metal salt of an aliphatic carboxylic acid or of an alkyl phenol in an amount within the range from about 25 to about 45 parts by weight; plus any one or more of the following optional ingredients:
(d) free aliphatic carboxylic acid in an amount within the range from about 0.5 to about 5 parts by weight; and
(e) acid phosphite in an amount within the range from about 0.5 to about 5 parts by weight.

In addition, any of the conventional polyvinyl chloride resin additives, such as lubricants, emulsifiers, antistatic agents, flame-proofing agents, pigments and fillers, can be employed.

Preferably, the stabilizer system is added to the polyvinyl chloride resin in an amount to provide in the resin from about 0.2 to about 1% of the phosphite; from about 0.1 to about 2% of phenolic antioxidant; and from about 0 to about 1% total of one or more of the additional ingredients, as noted above.

The stabilizer system is incorporated in the polymer in suitable mixing equipment, such as a mill or a Banbury mixer. Mixing is continued until the mixture is substantially uniform. The resulting composition is then removed from the mixing equipment and brought to the size and shape desired for marketing or use.

The stabilized polyvinyl chloride resin can be worked into the desired shape, such as by milling, calendering, extrusion or injection molding, or fiber-forming. In such operations, it will be found to have a considerably improved resistance to discoloration and embrittlement on exposure to heat and light.

The phosphite and amine stabilizer compositions of the invention are especially effective heat stablizers for olefin polymers such as polyethylene, polypropylene, polybutylene, polpentylene, polyisopentylene, and higher polyolefins, and copolymers of two or more olefins.

Olefin polymers on exposure to elevated temperatures undergo degradation, resulting in embrittlement and discoloration.

The phosphite and amine stabilizer compositions can be employed with any olefin polymer, including low-density polyethylene, high density polyethylene, polyethylenes prepared by the Ziegler-Natta process, copolymers of ethylene with minor amounts of propylene butene-1, hexene-1, n-octene-1, including so-called linear low density polyethylene, polypropylene prepared by the Ziegler-Natta process, and by other polymerization methods from propylene, poly(butene-1), poly(pentene-1, poly(3-methylbutene-1), poly(4-methylpentene-1), polystyrene, and mixtures of polyethylene and polypropylene with other compatible polymers, such as mixtures of polyethylene and polypropylene, and all copolymers of such olefins, such as copolymers of ethylene, propylene, and butene, with each other and with other copolymerizable monomers. The term "olefin polymer" encompasses both homopolymers and copolymers.

The preferred olefin polymers in which the phosphite amine compositions of this invention are effective include polypropylene manufactured by the catalytic polymerization of propylene and having a density of 0.880 to 0.913 g/ml and a melting point or softening point from 160° to 180° C.; polyethylene manufactured by the catalytic polymerization of ethylene and having a density of 0.85 to 1.00 g/ml and a 5.5% maximum extractable fraction in n-hexane at 50° C.; poly(methylpentene) manufactured by the catalytic polymerization of 4-methylpentene-1 and having a density of 0.82 to 0.85 g/ml and a melting point from 235° to 250° C., olefin copolymers manufactured by the catalytic copolymerization of two or more 1-alkenes having 2 to 8 carbons (except 4-methylpentene-1) having a density of 0.85 to 1.0 and a 5.5% maximum extractable fraction in n-hexane at 50° C; and copolymers of 4-methylpentene-1 and a 1-alkene having 6 to 10 carbon atoms having a density of 0.82 to 0.85 g/ml and a melting point of 235° to 250° C.

The phosphite and amine stabilizer compositions are also effective to enhance the resistance to heat degradation of polystyrene; polydienes, such as polybutadiene and polyisoprene; and copolymers of olefins and dienes with other ethylenically and acetylenically unsaturated monomers, such as ethylene-vinyl acetate copolymers, styrene-butadiene copolymers, acrylonitrile-styrene-butadiene copolymers, synthetic rubbers of all types, such as polychloroprene; polyvinylidene chloride; and copolymers of vinyl chloride and vinylidene chloride; vinylidene chloride and vinyl acetate; and other ethylenically unsaturated monomers; polyacetals such as polyoxymethylene and polyoxyethylene; polycarbonates; polyphenylene oxides; polyesters such as polyethylene glycolterephthalic acid ester polymers; polyamides such as polyepsilon-caprolactam; polyhexamethylene adipamide and polydecamethylene adipamide; polyurethanes; and epoxy resins.

The synthetic polymer can be in any physical form, including, for example, filaments, yarns, films, sheets, molded articles, latex and foam.

A sufficient amount of the stabilizer composition including the phosphite and amine is used to improve the resistance of the synthetic polymer to deterioration in physical properties, including, for example, discoloration, objectionable change in melt viscosity and embrittlement, under the conditions to which the polymer will be subjected. Very small amounts are usually adequate. Amounts within the range from about 0.001 to about 5% total stabilizers by weight of the polymer are satisfactory. Preferably, from 0.01 to 3% is employed, for optimum stabilization.

The phosphite and amine compositions of the invention can be employed as the sole stablizers or in combination with other conventional heat and light stabilizers for the particular olefin polymer.

Thus, for example, there can be employed fatty acid salts of polyvalent metals, and the higher fatty alkyl esters of thiodipropionic acids, such as, for example, dilauryl thiodipropionate.

With polyamide resin compositions, polyamide stabilizers such as copper salts in combination with iodides and/or other phosphorus compounds and salt of divalent manganese can be used.

With synthetic rubbers and acrylonitrile-butadiene-styrene terpolymers, polyvalent metal salts of higher fatty acids can be used.

In addition, other conventional additives for synthetic polymers, such as plasticizers, lubricants, emulsifiers, antistatic agents, flame-proofing agents, pigments and fillers, can be employed.

The stabilizer composition is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizers. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples represent preferred embodiments of synthetic resin compositions containing phosphite amine compositions of the invention.

EXAMPLE 12

Polyvinyl chloride resin compositions having the following formulation were prepared:

|  | Parts by Weight | |
|---|---|---|
|  | Example 12 | Control |
| Vinyl chloride homopolymer (Geon 110 × 450) | 100 | 100 |
| Dialkyl phthalate (Santicizer 711) | 43 | 43 |
| Epoxysoybean oil | 7 | 7 |
| Phosphite/amine composition of Example 3 | 0.2 | — |
| Zinc stearate | 0.15 | 0.25 |
| Calcium stearate | 0.12 | 0.19 |
| 2,6-di-t-butyl-p-cresol | 0.038 | 0.06 |

The compositions were milled on a two-roll mill at 350° F. for three minutes, and then sheeted off. The milled sheets were cut into strips, which were then placed in an oven and heated at 350° (177° C.) or 375° F. (190° C.) until dark edges appeared on the samples. Samples of each were cut off from the strips at 10 minute intervals, and placed on a card. The times required for the samples to yellow and to develop dark edges were noted, and are reported below in Table IV.

|  | Example 12 | Control |
|---|---|---|
| Oven heat stability 350° F. | | |
| Minutes to yellow | 90 | 15 |
| Minutes to dark edge | >120 | 120 |
| Oven heat stability 375° F. | | |
| Minutes to yellow | 30 | 10 |
| Minutes to dark edge | 70 | 50 |

Samples also were molded into panels 0.050 inch thick, and the yellow index determined according to ASTM D 1925-70 using a Hunter colorimeter and the following results:

|  | Example 12 | Control |
|---|---|---|
| Color of 0.050" molding, Hunter colorimeter | | |
| Yellow index, ASTM D 1925-70 | 2.02 | 3.94 |

The lower Yellow Index values signify less yellow and hence preferable samples. Example 5 is clearly superior.

EXAMPLE 13

Polypropylene compositions were prepared, having the following formulation:

|  | Parts by Weight | |
|---|---|---|
|  | Example 13 | Control |
| Polypropane (Profax 6501) | 100 | 100 |
| Calcium stearate | 0.1 | 0.1 |
| Phosphite amine composition of Example 3 | 0.05 | — |

The additives were blended with the polypropylene powder in a hexane slurry, and the hexane removed under vacuum in a rotary evaporator. The resulting blend was fed to an extruder, from which the material exited as a continuous strand. This was passed through a water cooling bath and chopped into pellets, which were collected and reextruded for a total of seven successive extrusions for each sample. In the first extrusion, the following temperature profile was used:
Zone 1—375° F.
Zone 2—410° F.
Zone 3—450° F.
Die—450° F.

In the subsequent extrusions, all zones were at 450° F.

Samples were taken from the first, third, fifth and seventh extrusion and molded into 0.02 inch (0.5 mm) thick panels. The melt flow index (MI, ASTM D 1238) and color (Hunter colorimeter yellow index, YI, ASTM D 1925) was determined for each sample. The results are tabulated in Table V.

TABLE V

| Stabilizer | Control 1 None | Control 2 TNPP[1] without amine | Control 3 TNPP[1] + 1% TIPA[2] | Example 13 TNPP[1] + 5% tallow-alkyl diethanolamine |
|---|---|---|---|---|
| First extrusion | | | | |
| MI | 3.2 | 1.8 | 1.2 | 1.5 |
| YI | 9.1 | 12.6 | 12.2 | 6.5 |
| 3rd extrusion | | | | |
| MI | 3.3 | 3.7 | 2.7 | 1.9 |
| YI | 13.5 | 10.8 | 13.5 | 11.3 |
| 5th extrusion | | | | |
| MI | 4.4 | 4.0 | 3.7 | 2.2 |
| YI | 14.0 | 10.7 | 16.1 | 12.3 |
| 7th extrusion | | | | |
| MI | 5.6 | 5.6 | 4.6 | 3.0 |
| YI | 13.6 | 12.0 | 15.2 | 12.0 |

Both MI and YI are desirably as low as possible. It can easily be seen that only Example 13, the sample containing TNPP with the tallow diethanolamine additive is consistently better in both MI and YI than a control without phosphite (left hand column) while TNPP without amine or with TIPA added is at best marginally effective and somewhat inconsistent.

EXAMPLES 14 to 18

Linear low-density polyethylene compositions were prepared having the following formulation:

| | Parts by Weight | |
|---|---|---|
| | Examples 14 to 18 | Control |
| Linear low-density polyethylene (Dow LLDPE, density 0.919, melt index 1.1) | 100 | 100 |
| Calcium stearate | 0.02 | 0.02 |
| Phosphite amine composition of Example 3 | As shown in Table VI | none |
| Phenolic antioxidants listed in Table VI | 0.025 (when present) | none |

The additives were blended with the linear low-density polyethylene granules in a hexane slurry, and the hexane removed under vacuum in a rotary evaporator. The resulting blend was fed to an extruder, from which the material exited as a continuous strand. This was passed through a water cooling bath and chopped into pellets, which were collected and reextruded for a total of seven successive extrusions for each sample. In the first extrusion, the following temperature profile was used:
Zone 1—360° F.
Zone 2—380° F.
Zone 3—400° F.
Die—400° F.

In the subsequent extrusions, all zones were at 430° F.

Samples were taken from the first, third, fifth and seventh extrusion and molded into 0.02 inch (0.5 mm) thick panels. The 190° C. melt index (MI, ASTM D 1238) and color (Hunter colorimeter yellow index, YI, ASTM D 1925) was determined for each sample. The results are tabulated in Table VI.

TABLE VI

| Example | Phosphite-Amine Composition, Parts by Weight | Phenolic Antioxidant | Extrusion No. | | | | | | | |
|---|---|---|---|---|---|---|---|---|---|---|
| | | | 1 | | 3 | | 5 | | 7 | |
| | | | MI | YI | MI | YI | MI | YI | MI | YI |
| Control | none | none | 0.86 | −4.1 | 0.53 | −1.1 | 0.46 | 2.6 | 0.40 | 5.2 |
| 14 | 0.05 | none | 0.99 | −0.53 | 0.83 | +7.0 | 0.69 | 9.5 | 0.63 | 8.9 |
| 15 | 0.025 | A 0.025 | 1.0 | −2.5 | 0.90 | 3.9 | 0.85 | 13.6 | 0.83 | 19.3 |
| 16 | 0.025 | B 0.025 | 1.0 | −0.18 | 0.99 | 3.3 | 1.0 | 5.1 | 1.0 | 7.8 |
| 17 | 0.025 | C 0.025 | 1.0 | −2.1 | 0.79 | 3.0 | 0.62 | 3.3 | 0.54 | 5.3 |
| 18 | 0.025 | D 0.025 | 1.0 | −2.9 | 0.99 | −0.41 | 0.88 | 3.5 | 0.79 | 4.9 |

Phenolic Antioxidants:
A = 2,2'-ethylidenebis(4,6-di-t-butylphenol)
B = 1,3,5-tris(4-t-butyl-3hydroxy-2,6-dimethylbenzyl)-1,3,5-tri-azine-2,4,5(1H,3H,5H)trione
C = Octadecyl 3,5-di-t-butyl-4-hydroxy hydrocinnannate
D = Pentaerythrityl tetrakis (3,5-di-t-butyl-4-hydroxy hydrocinnannate Unlike polypropylene, linear low-density polyethylene degrades by cross-linking and, as a result, the melt index decreases. The effectiveness of the phosphite-amine composition in Example 14, and of the combinations thereof with phenolic antioxidants in Examples 15 to 18 in minimizing this decrease is evident from the results presented. At the same time, good color protection is also obtained with the compositions of this invention.

Having regard to the foregoing disclosure the following is claimed as the inventive and patentable embodiments thereof:

1. Tris-organophosphite compositions having an improved hydrolytic stability, comprising
(1) a tris-organophosphite of the formula:

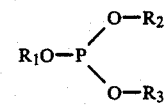

wherein:

$R_1$, $R_2$ and $R_3$ are selected from the group consisting of alkyl, alkenyl, aryl, alkylaryl and aralkyl groups together aggregating at least fourteen carbon atoms up to about sixty carbon stoms; and (2) a long-chain aliphatic amine in an amount to improve the hydrolytic stability of the phosphite and having the formula:

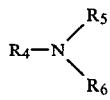

II wherein:

$R_4$, $R_5$ and $R_6$ are selected from the group consisting of hydrogen; aliphatic groups having from one to about thirty-six carbon atoms; and hydroxyalkyl having from two to about six carbon atoms; one of $R_4$, $R_5$ and $R_6$ is an aliphatic group having at least ten carbon atoms, and the remaining of $R_4$, $R_5$ and $R_6$ are selected from hydrogen, alkyl having from one to four carbon atoms and hydroxyalkyl.

2. Tris-organophosphite compositions according to claim 1 in which $R_1$, $R_2$ and $R_3$ are alkyl.

3. Tris-organophosphite compositions according to claim 1 in which $R_1$, $R_2$ and $R_3$ are alkylaryl.

4. Tris-organophosphite compositions according to claim 3 in which $R_1$, $R_2$ and $R_3$ are nonylphenyl.

5. Tris-organophosphite compositions according to claim 1 in which the amine is an aliphatic hydrocarbyl amine.

6. Tris-organophosphite compositions according to claim 1 in which the amine is an aliphatic amine having at least one hydroxyalkyl group.

7. Tris-organophosphite compositions according to claim 1 in which the amine is an aliphatic amine wherein one of $R_4$, $R_5$ and $R_6$ is hydrogen.

8. Tris-organophosphite compositions according to claim 1 in which the amine is an aliphatic amine wherein two of $R_4$, $R_5$ and $R_6$ are hydrogen.

9. Tris-organophosphite compositions according to claim 1 in which the amine is an aliphatic amine wherein one of $R_4$, $R_5$ and $R_6$ is alkyl of one to four carbon atoms.

10. Tris-organophosphite compositions according to claim 1 in which the amine is an aliphatic amine wherein two of $R_4$, $R_5$ and $R_6$ are alkyl of one to four carbon atoms.

11. Tris-organophosphite compositions according to claim 1 in which the amine is an aliphatic amine having two hydroxyalkyl groups.

12. Tris-organophosphite compositions according to claim 11 in which the hydroxyalkyl is hydroxyethyl.

13. Tris-organophosphite compositions according to claim 12 in which the amine is N-n-octadecyl diethanolamine.

* * * * *